(12) United States Patent
Leeah et al.

(10) Patent No.: US 10,952,962 B1
(45) Date of Patent: Mar. 23, 2021

(54) READY TO USE LIQUID FORMULATION

(71) Applicant: QuVa Pharma, Inc., Sugar Land, TX (US)

(72) Inventors: Travis A. Leeah, Sugar Land, TX (US); Jianping Chen, Sugar Land, TX (US)

(73) Assignee: QuVa Pharma, Inc., Sugar Land, TX (US)

(*) Notice: Subject to any disclaimer, the term of this patent is extended or adjusted under 35 U.S.C. 154(b) by 66 days.

(21) Appl. No.: 16/381,407

(22) Filed: Apr. 11, 2019

Related U.S. Application Data

(60) Provisional application No. 62/656,236, filed on Apr. 11, 2018.

(51) Int. Cl.

| | | |
|---|---|---|
| *A61K 9/08* | (2006.01) | |
| *A61P 23/00* | (2006.01) | |
| *A61K 9/00* | (2006.01) | |
| *A61K 31/137* | (2006.01) | |
| *A61K 31/167* | (2006.01) | |
| *A61K 47/02* | (2006.01) | |
| *A61K 47/12* | (2006.01) | |
| *A61K 47/18* | (2017.01) | |

(52) U.S. Cl.
CPC .............. *A61K 9/08* (2013.01); *A61K 9/0019* (2013.01); *A61K 31/137* (2013.01); *A61K 31/167* (2013.01); *A61K 47/02* (2013.01); *A61K 47/12* (2013.01); *A61K 47/183* (2013.01); *A61P 23/00* (2018.01)

(58) Field of Classification Search
CPC combination set(s) only.
See application file for complete search history.

(56) References Cited

U.S. PATENT DOCUMENTS

| 6,008,256 A * | 12/1999 | Haraguchi | ........... A61K 31/195 514/626 |
| 10,130,592 B2 * | 11/2018 | Kannan | ...................... A61P 9/06 |
| 2003/0216413 A1 | 11/2003 | Root-Bernstein et al. | |

FOREIGN PATENT DOCUMENTS

| CA | 2070724 A1 | 12/1993 |
| WO | 2010139752 A2 | 12/2010 |

OTHER PUBLICATIONS

Connors, K.A., et al., "Epinephrine", Drug Kinetics, Chemical Stability of Pharmaceuticals, A Handbook for Pharmacists, Second Edition; pp. 438-447 (1986).
Xylocaine® (lidocaine HCI Injection, USP) prescribing information, Nov. 2018.
Customer Letter from Fresenius Kabi regarding unavailability of Xylocaine® and Sensorcaine® products, dated Nov. 14, 2016.
Bernards, C.M., and D.J. Kopacz, "Effect of Epinephrine on Lidocaine Clearance In Vivo", Anesthesiology 91(4), pp. 962-968 (1999).
Sinnott, C.J., et al., "On the Mechanism by Which Epinephrine Potentiates Lidocaine's Peripheral Nerve Block", Anesthesiology, 98(1), pp. 181-188 (2003).
Grubstein, B., and E. Milano, "Stabilization of Epinephrine in a Local Anesthetic Injectable Solution Using Reduced Levels of Sodium Metabisulfite and EDTA", Drug Development and Industrial Pharmacy, 18(14), 1549-1566 (1992).
Kirchhoefer, R.D. et al., "Stabilty of sterile aqueous lidocaine hydrochloride and epinephrine injections submitted by U.S. hospitals", American Journal of Hospital Pharmacy, vol. 43, pp. 1736-1741 (1986).
Lidocaine HCI 2% and Epinephrine 1:100,000 Solution for Topical Iontophoretic System, FDA labeling, Approval Oct. 26, 2004, pp. 1-14.

* cited by examiner

*Primary Examiner* — Kortney L. Klinkel
*Assistant Examiner* — Tori Strong
(74) *Attorney, Agent, or Firm* — Daniel R. Evans; Melissa M. Hayworth

(57) ABSTRACT

Disclosed herein is a ready-to-use liquid formulation comprising lidocaine hydrochloride and epinephrine hydrochloride. Also disclosed herein is a process for preparing a ready-to-use liquid formulation comprising lidocaine hydrochloride and epinephrine hydrochloride, as well as methods for using the ready-to-use liquid formulation.

16 Claims, No Drawings

READY TO USE LIQUID FORMULATION

RELATED APPLICATION

The present application claims priority to U.S. Provisional Patent Application No. 62/656,236, filed on Apr. 11, 2018, herein incorporated by reference in its entirety.

FIELD OF THE INVENTION

Disclosed herein is a ready-to-use liquid formulation comprising lidocaine hydrochloride and epinephrine hydrochloride. Also disclosed herein is a process for preparing a ready-to-use liquid formulation comprising lidocaine hydrochloride and epinephrine hydrochloride, as well as methods for using the ready-to-use liquid formulation.

BACKGROUND

Lidocaine with Epinephrine 1:100,000 in water (saline) is an anesthetic solution used for local or regional anesthesia by infiltration techniques such as percutaneous injection, by peripheral nerve block techniques such as brachial plexus and intercostal and by central neural techniques such as lumbar and caudal epidural blocks. See, e.g., Bernards et al., *Effect of Epinephrine on Lidocaine Clearance In Vivo*, Anesthesiology (1999) 91(4): 962-968.

Many hospitals use Lidocaine with Epinephrine 1:100,000 to provide local anesthesia. The added epinephrine localizes the lidocaine in the in the tissue, thereby decreasing its clearance. Most manufactured lidocaine with epinephrine injections contain sodium metabisulfite at 0.5 mg-1 mg/mL and some will include citric acid. Multi-dose vials will include methylparaben (1 mg/mL) or other agents as antimicrobial preservative(s). The pH is adjusted to 4.5 (3.3-5.5). However, for this formula to keep epinephrine HCl stable (at this pH), the head space within the vial must be nitrogen gassed (remove oxygen).

In recent years, prolonged shortages of Lidocaine with Epinephrine 1:100,000 have created the need for an available supply of a ready-to-use formulation comprising lidocaine hydrochloride and epinephrine hydrochloride (e.g., packaged in a syringe).

DETAILED DESCRIPTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "optional" or "optionally" as used herein means that a subsequently described event or circumstance may but need not occur, and that the description includes instances where the event or circumstance occurs and instances in which it does not.

A first embodiment is directed to a ready-to-use liquid formulation comprising: lidocaine hydrochloride in an amount of about 10 mg/mL or about 20 mg/mL; epinephrine hydrochloride in an amount of about 10 mcg/mL, based on epinephrine free base; sodium chloride in an amount of about 7 mg/mL; sodium metabisulfite in an amount of about 5.2 mcg/mL; citric acid in an amount of about 0.2 mg/mL; ethylenediaminetetraacetic acid ("EDTA") sodium in an amount of about 0.2 mg/mL; a sufficient amount of sterile water for injection; and a sufficient amount of a pH adjuster to obtain a pH of about 3.4.

In a first aspect of the first embodiment, the pH adjuster is hydrochloric acid, sodium hydroxide, or a combination thereof.

In a second aspect of the first embodiment, the ready-to-use liquid formulation may be stored within a light-resistant container having a light transmission of less than 5%, less than 4%, less than 3%, less than 2%, or less than 1% at any wavelength between 290 nm and 450 nm. Said light-resistant container may comprise, for example, an amber-colored bag, film, or plastic.

A second embodiment is directed to a syringe comprising a ready-to-use liquid formulation comprising: lidocaine hydrochloride in an amount of about 10 mg/mL or about 20 mg/mL; epinephrine hydrochloride in an amount of about 10 mcg/mL, based on epinephrine free base; sodium chloride in an amount of about 7 mg/mL; sodium metabisulfite in an amount of about 5.2 mcg/mL; citric acid in an amount of about 0.2 mg/mL; ethylenediaminetetraacetic acid ("EDTA") sodium in an amount of about 0.2 mg/mL; a sufficient amount of sterile water for injection; and a sufficient amount of a pH adjuster to obtain a pH of about 3.4

In a first aspect of the second embodiment, the syringe contains about 5 mL of the ready-to-use liquid formulation.

In a second aspect of the second embodiment, the syringe contains about 10 mL of the ready-to-use liquid formulation.

In a third aspect of the second embodiment, each of lidocaine and epinephrine has a potency of at least 90% after storage for about 1.5-months to about 3-months at a temperature of about 25° C.

In a fourth aspect of the second embodiment, each of lidocaine and epinephrine has a potency of at least 90% after storage for about 3-months at a temperature of about 25° C.

A third embodiment is directed to a light-sensitive container comprising any one of the syringes of the second embodiment, wherein the light-sensitive container has a light transmission of less than 5%, less than 4%, less than 3%, less than 2%, or less than 1% at any wavelength between 290 nm and 450 nm. Said light-sensitive container may comprise, for example, an amber-colored bag, film, or plastic.

A fourth embodiment is directed to a ready-to-use liquid formulation consisting of: lidocaine hydrochloride in an amount of about 10 mg/mL or about 20 mg/mL; epinephrine hydrochloride in an amount of about 10 mcg/mL, based on epinephrine free base; sodium chloride in an amount of about 7 mg/mL; sodium metabisulfite in an amount of about 5.2 mcg/mL; citric acid in an amount of about 0.2 mg/mL; EDTA sodium in an amount of about 0.2 mg/mL; a sufficient amount of sterile water for injection; and a sufficient amount of a pH adjuster to obtain a pH of about 3.4.

In a first aspect of the fourth embodiment, the pH adjuster is hydrochloric acid, sodium hydroxide, or a combination thereof.

In a second aspect of the fourth embodiment, the ready-to-use liquid formulation may be stored within a light-resistant container having a light transmission of less than 5%, less than 4%, less than 3%, less than 2%, or less than 1% at any wavelength between 290 nm and 450 nm. Said light-resistant container may comprise, for example, an amber-colored bag, film, or plastic.

A fifth embodiment is directed to a syringe comprising a ready-to-use liquid formulation consisting of: lidocaine hydrochloride in an amount of about 10 mg/mL or about 20 mg/mL; epinephrine hydrochloride in an amount of about 10 mcg/mL, based on epinephrine free base; sodium chloride in an amount of about 7 mg/mL; sodium metabisulfite in an amount of about 5.2 mcg/mL; citric acid in an amount of about 0.2 mg/mL; EDTA sodium in an amount of about 0.2 mg/mL; a sufficient amount of sterile water for injection; and a sufficient amount of a pH adjuster to obtain a pH of about 3.4.

In a first aspect of the fifth embodiment, the syringe contains about 5 mL of the ready-to-use liquid formulations.

In a second aspect of the fifth embodiment, the syringe contains about 10 mL of the ready-to-use liquid formulation.

In a third aspect of the fifth embodiment, each of lidocaine and epinephrine has a potency of at least 90% after storage for about 1.5-months to about 3-months at a temperature of about 25° C.

In a fourth aspect of the fifth embodiment, each of lidocaine and epinephrine has a potency of at least 90% after storage for about 3-months at a temperature of about 25° C.

A sixth embodiment is directed to a light-sensitive container comprising any one of the syringes of the fifth embodiment, wherein the light-sensitive container has a light transmission of less than 5%, less than 4%, less than 3%, less than 2%, or less than 1% at any wavelength between 290 nm and 450 nm. Said light-sensitive container may comprise, for example, an amber-colored bag, film, or plastic.

A seventh embodiment is directed to a method for providing procedural analgesia to a patient in need thereof, which comprises: administering to the patient any one of the ready-to-use liquid formulations described in the first through sixth embodiments.

In a first aspect of the seventh embodiment, the procedural analgesia is associated with a venipuncture, a shave removal, or a punch biopsy.

An eighth embodiment is directed to a process for preparing any one of the ready-to-use liquid formulations of embodiments one through six, which comprises (or consists of): a) dissolving sodium chloride (43.4 g) and lidocaine hydrochloride in a first container including sterile water for injection; b) adding citric acid, EDTA sodium, and sodium metabisulfite in the first container of step a) and stirring to provide a dissolved solution; c) adding the pH adjuster to the first container of step b) to obtain a pH of the solution of 2.5; d) dissolving epinephrine in the first container of step c); e) if necessary, adding 10% v/v hydrochloric acid to the first container of step d) to maintain the pH of the solution below 3.0; f) adding an additional amount of sterile water to the first container of step e) and adding the pH adjuster to obtain a pH of from about 3.5; g) transferring the solution of step f) to a second container; and h) filtering the solution of step g) through a 0.22 micron filter.

A ninth embodiment is directed to a syringe comprising about 5 mL of the ready-to-use liquid formulation prepared by the process of the sixth embodiment.

In a first aspect of the ninth embodiment, the syringe contains about 5 mL of the ready-to-use liquid formulations.

In a second aspect of the ninth embodiment, the syringe contains about 10 mL of the ready-to-use liquid formulation.

In a third aspect of the ninth embodiment, each of lidocaine and epinephrine has a potency of at least 90% after storage for about 1.5-months to about 3-months at a temperature of about 25° C.

In a fourth aspect of the ninth embodiment, each of lidocaine and epinephrine has a potency of at least 90% after storage for about 3-months at a temperature of about 25° C.

A tenth embodiment is directed to a light-sensitive container comprising any one of the syringes of the ninth embodiment, wherein the light-sensitive container has a light transmission of less than 5%, less than 4%, less than 3%, less than 2%, or less than 1% at any wavelength between 290 nm and 450 nm. Said light-sensitive container may comprise, for example, an amber-colored bag, film, or plastic.

EXAMPLES

BD syringes described herein are available commercially from Becton, Dickinson and Company. The BD syringes are fitted with a Luer-Lok tip and have volumes (in mL) of: 1, 3, 5, 10, 20, 30, and 60.

Ultra Performance Liquid Chromatography (UPLC) was used for purposes of identification and potency determinations.

|  | Lidocaine HCl | Epinephrine |
| --- | --- | --- |
| Equipment: | Waters Acquity H Class UPLC with UV Detector (or equivalent) | Waters Acquity H Class UPLC with UV Detector (or equivalent) |
| Column: | Luna 5 μm C18(2) 100A, 150X4.6 mm column | Luna 5 μm C18(2) 100A, 150X4.6 mm column |
| Column Temperature: | 40.0° C. | 40.0° C. |
| Flow Rate: | 0.4 mL/min | 1.0 mL/min |
| Injection Volume: | 1 μL | 10 μL |
| UV Detector: | 254 nm | 220 nm |
| Run Time: | About 5 minutes | 30 minutes |
| Seal Wash, Purge, and Wash: | 90:10 Purified Water:Acetonitrile | 50:50 Water:Methanol |
| Mobile Phase A: | 90:10 pH 3.0 Buffer:Acetonitrile | pH 3.0 buffer |
| Mobile phase B: | Methanol | Methanol:Acetonitrile 250:50 |
| Gradient: | N.A. Isocratic: 95% A\|5% B | 0 min: 70% A\|30% B<br>6 min: 70 A\|30 B<br>10 min: 40% A\|60% B<br>24 min: 20% A\|80% B<br>25 min: 70% A\|30% B<br>30 min: 70% A\|30% B |

Phosphate Buffer Preparation (for Lidocaine HCl): Dissolve 1.4 g of Potassium Phosphate Monobasic in 1000 ml of purified water and mix well. Adjust the pH of the buffer with phosphoric acid to pH 3.0.

Mobile Phase A (for Lidocaine HCl): Mix 900 ml of Phosphate Buffer and 100 ml of Acetonitrile. Filter using 0.2 μm filter, degas.

Phosphate Buffer Preparation (for Epinephrine): Dissolve 1.1 g of 1-Heptanesulfonic acid Sodium Salt in 1000 mL of purified water and mix well. Adjust the pH of the buffer with Phosphoric acid to pH 3.0.

Potency assays used working standard solutions for Lidocaine HCl and Epinephrine Bitartrate. The concentration of working standard solution is about 10 mcg/mL for Epinephrine. The concentration of Lidocaine HCl in the working standard solution is about 0.1 mg/mL for Lidocaine HCl (or about 0.09 mg/mL for Lidocaine).

Calculate the Potency of Lidocaine HCl as Follows:

$$\text{Lidocaine HCl Potency (\%)} = \frac{As}{Astd} \times C \times DF \times \frac{P}{100} \times CF \times \frac{1}{LC} \times 100$$

Where
As is the UPLC peak area of lidocaine (elution time of about 2.3 min);
Astd is the average UPLC peak area (N=5) of lidocaine from working standard solution;
C is the working standard concentration of Lidocaine HCl, about 0.1 mg/mL for Lidocaine HCl (or about 0.09 mg/mL for Lidocaine);

DF is a dilution factor (DF=0.005 for 2% w/v Lidocaine HCl composition and DF=0.01 for 1% w/v Lidocaine HCl composition); and
P is the Standard potency, % (obtained by comparison to standard solution);
CF is the correction factor (CF=1 when Lidocaine HCl standard is used and CF=1.1556), which is the ratio of the molecular weight of Lidocaine HCl (270.80) to the molecular weight of Lidocaine (234.34); and
LC is the Label Claim of the Lidocaine HCl in the LE composition, 10 mg/mL.
Calculate the Potency of Epinephrine as Follows:

$$\text{Epinephrine Potency (\%)} = \frac{As}{Astd} \times C \times \frac{P}{100} \times \frac{1}{LC} \times CF \times 100$$

Where
As is the UPLC peak area of epinephrine (elution time of about 4.1 min);
Astd is the average UPLC area (N=5) of epinephrine from working standard solution;
C is the working standard solution concentration of Epinephrine Bitartrate, about 10 mcg/mL;
P is the standard potency, % (obtained by comparison to standard solution);
CF is the correction factor (0.54969), which is the ratio of the molecular weight of epinephrine (183.207) to the molecular weight of epinephrine bitartrate (333.29); and
LC is the Label Claim of the Epinephrine base in LE composition, 10 mcg/mL.

Examples 1-6. Evaluation of Epinephrine Content with Varying Amounts of Sodium Metabisulfite with or without Sodium EDTA

|  | Examples | | | | | |
| --- | --- | --- | --- | --- | --- | --- |
|  | 1 | 2 | 3 | 4 | 5 | 6 |
| Lidocaine HCl (mg/mL) | 10 | 10 | 10 | 10 | 10 | 10 |
| Epinephrine (mcg/mL) | 10 | 10 | 10 | 10 | 10 | 10 |
| Sodium Chloride (mg/mL) | 7 | 7 | 7 | 7 | 7 | 7 |
| Sodium Metabisulfite (mg/mL) | 0.5 | 0.5 | 0.5 | 0.5 | 1 | 1 |
| Citric Acid (mg/mL) | 0.2 | — | 0.2 | 0.2 | 0.2 | 0.2 |
| SWFI | q.s. | q.s. | q.s. | q.s. | q.s. | q.s. |
| pH | 4.0 | 4.0 | 4.5 | 5.0 | 4.5 | 3.4 |
| Epinephrine Potency (%) | | | | | | |
| Day 8 | 86.1[a] | 71.7 | 89.2 | 82.6 | 93.8 | 86.7 |

[a] Epinephrine Potency measured at Day 6

The compositions were stored at 40° C. in a 5 mL BD syringe, and were evaluated by UPLC for epinephrine potency on the eighth day of after the manufacture date—except for Example 1, which was evaluated on the sixth day after manufacture. The results for accelerated testing plainly showed that the compositions of Examples 1-6 have a limited shelf life.

Examples 7-15. Evaluation of Epinephrine Content with Varying Amounts of Sodium Metabisulfite with or without EDTA Disodium Dihydrate (i.e., EDTA Sodium)

|  | Examples | | | | | | | | |
| --- | --- | --- | --- | --- | --- | --- | --- | --- | --- |
|  | 7 | 8 | 9 | 10 | 11 | 12 | 13 | 14 | 15 |
| Lidocaine HCl (Anhydrous), mg/mL | 10 | 10 | 10 | 10 | 10 | 10 | 10 | 10 | 10 |
| Epinephrine (base), mcg/mL | 10 | 10 | 10 | 10 | 10 | 10 | 10 | 10 | 10 |
| Sodium Chloride, mg/mL | 7 | 7 | 7 | 7 | 7 | 7 | 7 | 7 | 7 |
| Sodium Metabisulfite, mcg/mL | 1.03 | 2.6 | 5 | 14 | 50 | 260 | 520 | 1030 | 5 |
| Citric Acid (anhydrous), mg/mL | 0.2 | 0.2 | 0.2 | 0.2 | 0.2 | 0.2 | 0.2 | 0.2 | 0.2 |
| EDTA Sodium, mg/mL | N/A | N/A | N/A | N/A | N/A | N/A | N/A | N/A | 0.2 |
| SWFI, mL | 100 | 100 | 200 | 200 | 100 | 100 | 100 | 100 | 200 |
| pH | 3.47 | 3.4 | 3.43 | 3.47 | 3.36 | 3.44 | 3.47 | 3.45 | 3.38 |
| Epinephrine Potency (%) | | | | | | | | | |
| Day 3, 40° C. | 94.6 | 97 | 100.8 | 100 | 98 | 92.3 | 89.3 | 88.6 | 102.6 |
| Day 23, 40° C. | — | — | — | — | — | — | — | — | 95.4 |

Of the nine formulations, Example 15 exhibited the highest epinephrine potency. Based on the accelerated data for the Example 15 composition, it is estimated that such a formulation would exhibit a shelf life of about 6-mo to 1-year (when stored at 5° C.) and 1.5-mo to 3-mo (when stored at 25° C.). The estimated shelf life is surprising considering that no effort was made to exclude air from the compositions. This is surprising since epinephrine oxidizes to adrenochrome in the presence of air. This also is surprising considering that dissolved oxygen may be present in water in an amount of about 9 mg/L, which corresponds to a molar amount of oxygen that exceeds the molar amount of epinephrine by about 5-fold.

Based on the stability results of the Example 15 composition, two compositions (containing either 1% w/v Lidocaine HCl (L1) or 2% w/v Lidocaine HCl (L2)) are contemplated.

| Exemplary Compositions | L1 | L2 |
| --- | --- | --- |
| Lidocaine HCl (Anhydrous), mg/mL | 10 | 20 |
| Epinephrine (base), mcg/mL | 10 | 10 |
| Sodium Chloride, mg/mL | 7 | 7 |
| Sodium Metabisulfite, mcg/mL | 5.2 | 5.2 |
| Citric Acid (anhydrous), mg/mL | 0.2 | 0.2 |
| EDTA Sodium, mg/mL | 0.2 | 0.2 |
| 10% w/v HCl and/or | q.s. (pH 3.4) | |

-continued

| Exemplary Compositions | L1 | L2 |
|---|---|---|
| 10% w/v NaOH SWFI, mL | 100 | 100 |

Example 16: Preparation of Ready-to-Use Liquid Formulation Containing LE (Lidocaine 1% w/v)

1. Wrap a first container with amber bag for light protection (the bag has a light transmission less than 5% at any wavelength between 290 nm and 450 nm). Add 4900-5000 mL (~80% final volume) sterile water for injection ("SWFI") in the container.
2. Add following powders under stirring and mixing to dissolve in the first container: Sodium Chloride (43.4 g) and Lidocaine HCl (monohydrate) (66.10 g). Use 132.2 g of Lidocaine HCl (monohydrate) for Lidocaine HCl 2% w/v.
3. Add the following powders under stirring and mixing to dissolve in the first container: Citric Acid (1.24 g), EDTA Sodium (1.24 g), and Sodium Metabisulfite (31.93 mg). Alternatively, add the following powders under stirring and mixing to dissolve in the first container Citric Acid (1.24 g) and EDTA Sodium (1.24 g), along with a sufficient volume (e.g., about 12.5 mL) of sodium metabisulfite (2.56 mg/mL) to provide a final sodium metabisulfite concentration of 5.2 mcg/mL.
4. Adjust pH to 2.5 using 10% w/v hydrochloric acid (HCl) and 10% w/v sodium hydroxide (NaOH).
5. Add Epinephrine Base 62.0 mg with constant stirring and mix to dissolve for a minimum 30 minutes.
6. Check pH and ensure that the pH is below 3.0.
7. If necessary, add additional 10% w/v HCl to maintain pH below 3.0.
8. QS to 5600 ml (~90% final volume) with SWFI.
9. Adjust pH to 3.4 (3.3-3.5) using 10% HCl and/or 10% NaOH.
10. QS to 6200 mL with SWFI. Mixing for 5 minutes.
11. Transfer 3100 mL into 3 L bag.
13. Filter the solution using polyethersulfone filter (0.22 μm).
14. Fill 5 mL of solution in each 5 mL syringe.

The syringe may be protected from light by storage in a container having a light transmission of less than 5%, less than 4%, less than 3%, less than 2%, or less than 1% at any wavelength between 290 nm and 450 nm. (See, e.g., USP 40<671> for a procedure for determining spectral transmission of a container.)

The syringed products are tested for potency, stability, sterility, and endotoxin content, as shown below.

| Analysis | Specification | Test Method |
|---|---|---|
| Potency | 90.0-110.0%. for both Lidocaine and Epinephrine | Potency/Purity Analytical Testing Method (see UPLC methods) |
| Sterility[1] | Sterile | USP <71> |
| Endotoxin | ≤0.148 EU/ml | USP <85> |

Sterility[1]: it meets or exceeds USP <71> requirements. Where no microorganism growth, test result is reported as "Sterile"; otherwise, report the detected microorganism colony forming units (CFU).

Stability testing shows that the ready-to-use formulation has a stability such that each of lidocaine and epinephrine has a potency of at least 90% after storage for about 3-months at a temperature of about 25° C.

The subject matter of U.S. Provisional Patent Application No. 62/656,236, filed on Apr. 11, 2018, is incorporated by reference. Information disclosed in the related application and the references cited herein is incorporated by reference in its entirety. In the event that information incorporated by reference conflicts with the meaning of a term or an expression disclosed herein, the meaning of the term or the expression disclosed herein controls.

The invention claimed is:

1. A ready-to-use liquid formulation comprising:
   lidocaine hydrochloride in an amount of about 10 mg/mL or about 20 mg/mL;
   epinephrine hydrochloride in an amount of about 10 mcg/mL, based on epinephrine free base;
   sodium chloride in an amount of about 7 mg/mL;
   sodium metabisulfite in an amount of about 5.2 mcg/mL;
   citric acid in an amount of about 0.2 mg/mL;
   EDTA sodium in an amount of about 0.2 mg/mL;
   a sufficient amount of sterile water for injection; and
   a sufficient amount of a pH adjuster to obtain a pH of about 3.4.

2. The ready-to-use liquid formulation of claim 1, wherein the pH adjuster is hydrochloric acid, sodium hydroxide, or a combination thereof.

3. A syringe containing about 5 mL of the ready-to-use liquid formulation of any one of claim 1.

4. The syringe of claim 3, wherein each of lidocaine and epinephrine has a potency of at least 90% after storage for about 3-months at a temperature of about 25° C.

5. A light-sensitive container comprising the syringe of claim 3, wherein the light sensitive container has light transmission of less than 5% at any wavelength between 290 nm and 450 nm.

6. A ready-to-use liquid formulation consisting of:
   lidocaine hydrochloride in an amount of about 10 mg/mL or about 20 mg/mL;
   epinephrine hydrochloride in an amount of about 10 mcg/mL, based on epinephrine free base;
   sodium chloride in an amount of about 7 mg/mL;
   sodium metabisulfite in an amount of about 5.2 mcg/mL;
   citric acid in an amount of about 0.2 mg/mL;
   EDTA sodium in an amount of about 0.2 mg/mL;
   a sufficient amount of sterile water for injection; and
   a sufficient amount of a pH adjuster to obtain a pH of about 3.4.

7. The ready-to-use liquid formulation of claim 6, wherein the pH adjuster is hydrochloric acid, sodium hydroxide, or a combination thereof.

8. A syringe containing about 5 mL of the ready-to-use liquid formulation of any one of claim 6.

9. The syringe of claim 8, wherein each of lidocaine and epinephrine has a potency of at least 90% after storage for about 3-months at a temperature of about 25° C.

10. A light-sensitive container comprising the syringe of claim 8, wherein the light-sensitive container has a light transmission of less than 5% at any wavelength between 290 nm and 450 nm.

11. A method for providing procedural analgesia to a patient in need thereof, which comprises:
   administering the ready-to-use liquid formulation of claim 1 to the patient.

12. The method of claim 11, wherein the procedural analgesia is associated with a venipuncture, a shave removal, or a punch biopsy.

13. A process for preparing the ready-to-use liquid formulation of claim 1, which comprises:

a) dissolving sodium chloride (43.4 g) and lidocaine HCl in a first container including sterile water for injection;
b) adding citric acid, EDTA sodium, and sodium metabisulfite in the first container of step a) and stirring to provide a dissolved solution;
c) adding the pH adjuster to the first container of step b) to obtain a pH of the solution of 2.5;
d) dissolving epinephrine in the first container of step c);
e) if necessary, adding 10% v/v hydrochloric acid to the first container of step d) to maintain the pH of the solution below 3.0;
f) adding an additional amount of sterile water to the first container of step e) and adding the pH adjuster to obtain a pH of from about 3.5;
g) transferring the solution of step f) to a second container; and
h) filtering the solution of step g) through a 0.22 micron filter.

14. A syringe product containing about 5 mL of the ready-to-use liquid formulation prepared by the process of claim 13.

15. The syringe of claim 14, wherein each of lidocaine and epinephrine has a potency of at least 90% after storage for about 3-months at a temperature of about 25° C.

16. A light-sensitive container comprising the syringe of claim of claim 14, wherein the light-sensitive container has a light transmission of less than 5% at any wavelength between 290 nm and 450 nm.

* * * * *

UNITED STATES PATENT AND TRADEMARK OFFICE
CERTIFICATE OF CORRECTION

PATENT NO. : 10,952,962 B1
APPLICATION NO. : 16/381407
DATED : March 23, 2021
INVENTOR(S) : Travis A. Leeah and Jianping Chen It is certified that error appears in the above-identified patent and that said Letters Patent is hereby corrected as shown below:

In the Claims

Claim 16, Column 9, Lines 25 and 26 should read:
A light-sensitive container comprising the syringe of claim 14, wherein the light-sensitive container has Signed and Sealed this
Eighteenth Day of May, 2021

Drew Hirshfeld
*Performing the Functions and Duties of the
Under Secretary of Commerce for Intellectual Property and
Director of the United States Patent and Trademark Office*